US005962769A

United States Patent [19]

Albertsen et al.

[11] Patent Number: 5,962,769
[45] Date of Patent: Oct. 5, 1999

[54] INDUCTION OF MALE STERILITY IN PLANTS BY EXPRESSION OF HIGH LEVELS OF AVIDIN

[75] Inventors: Marc C. Albertsen, West Des Moines, Iowa; John A. Howard, College Station, Tex.; Sheila Maddock, Johnston, Iowa

[73] Assignee: Pioneer Hi-Bred International, Inc., Des Moines, Iowa

[21] Appl. No.: 08/893,049

[22] Filed: Jul. 14, 1997

Related U.S. Application Data

[63] Continuation-in-part of application No. 08/475,582, Jun. 7, 1995, abandoned.

[51] Int. Cl.$^6$ .............................. A01H 5/00; A01H 1/02; C12N 15/12; C12N 15/82
[52] U.S. Cl. ...................... 800/303; 800/274; 800/281; 800/284; 800/286; 800/287; 800/288; 800/298; 800/306; 800/312; 800/320.1; 800/322; 435/69.1; 435/69.7; 435/69.8; 435/320.1; 435/468; 536/23.5; 536/24.1; 536/23.7; 536/24.5
[58] Field of Search ................................ 536/23.5, 24.1, 536/24.5, 23.7; 800/205, DIG. 14, 26, 56, 274, 281, 284, 286, 287, 288, 298, 303, 306, 312, 320.1, 322; 435/69.1, 172.3, 69.7, 69.8, 320.1, 468; 47/58, DIG. 1

[56] References Cited

U.S. PATENT DOCUMENTS

| 5,349,122 | 9/1994 | Hain et al. ............................... 800/205 |
| 5,356,799 | 10/1994 | Fabinjanski et al. ................. 435/172.3 |

FOREIGN PATENT DOCUMENTS

| 0 342 926 | 11/1989 | European Pat. Off. . |
| 0 412 006 | 2/1991 | European Pat. Off. . |
| WO 86/02077 | 4/1986 | WIPO . |
| WO 92/01370 | 2/1992 | WIPO . |
| WO 94/00992 | 1/1994 | WIPO . |
| WO 94/21804 | 9/1994 | WIPO . |
| WO 96/16182 | 5/1996 | WIPO . |
| WO 96/17945 | 6/1996 | WIPO . |
| WO 96/40925 | 12/1996 | WIPO . |
| WO 96/40949 | 12/1996 | WIPO . |
| WO 97/17455 | 5/1997 | WIPO . |

OTHER PUBLICATIONS

Smith et al. Nature 334: 724–726, Aug. 1988.
Evans et al. Biochem. Soc. Trans. 20: 3445, 1992.
Mazzolini et al. Plant Mol. Biol. 20: 715–731, 1992.
Gope et al. Nucl. Acids Res. 15(8): 3595–3606, 1987.
Morgan et al. Entomol. exp. appl. 69: 97–108, 1993.
Benfey et al. Science 250: 959–966, Nov. 1990.

Hood et al. "Commercial Production of Avidin from Transgenic Maize", In Vitro 32(3) Part II Mar. 1996, p. 67A, Abstract No. XP002035234.
Hood et al. Commercial Production of Avidin from Transgenic Maize: Characterization of Transformant, Production, Processing . . . , *Mol. Breeding* 3: 291–306 (1997).
Schmulling et al. "Restoration of Fertility by Antisense RNA in Genetically Engineered Male Sterile Tobacco Plants", *Mol. Gen. Genet.* 237: 385–394 (1993).
Huttner et al. A Ribozyme Gene to Restore Fertility in Artificially Male Strerile Plants, *J. Cellular Biochem.* Jan. 15, 1995, p. 220, Abstract No. XP002035923.
Airenne, et al. "Production of Recombinant Avidin in *Escherichia coli*", *Gene.*, 144: 75–80, (1994).
Bennett, et al. "Additional Mitosis in Wheat Pollen induced by Ethrel", *Nature* 240: 566–568 (1972).
Berhe, et al. "Studies of Ethephon as a Possible Selective Male Gametocide on Tef", *Crop Science* 18: 35–38 (1978).
Colhoun, et al. "The Cytological Effects of the Gametocides Ethrel and RH–531 on Microsporogenesis in Barley (*Hordeum vulgare* L. )", *Plant, Cell and Environ.* 6: 21–29 (1983).
Cross, et al. "Chemical Agents That Inhibit Pollen Development: Tools for Research", *Sex. Plant Reprod.* 4: 235–243 (1991).
Guan, et al. "Expression of Streptavidin Gene in Tobacco and its Effects on Bacteria", *Plant Physiol.* 102(1): 45, Abstract 234, Joint Annual Meeting of American Society of Plant Physiologists and Canadian Society of Plant Physiologists, Minneapolis, MN Jul. 21–Aug. 4, 1993.
Keinanen, et al. "Molecular Cloning and Nucleotide Sequence of Chicken Avidin–related Genes 1–5", *Eur. J. Biochem.* 220(2): 615–621 (1994).
Kulomaa, et al. "Production of Recombinant Avidin and Avidin–Fusion Proteins in Bacterial and Insect Cells", *The FASEB Journal*, 9:6 A1395, Abstract 802, Annual Meeting of American Society for Biochemistry and Molecular Biology, San Francisco, CA May 21–25, 1995.
Mariani, et al. "A Chimaeric Ribonuclease–inhibitor Gene Restores Fertility to Male Sterile Plants", *Nature* 357: 384–387 (1992).
Morgan et al. Avidin and Streptavidin as insecticidal and growth inhibiting dietary proteins, Abstract #29456, CABA 94, *Ent. Exp. Appl.* 69: 97–108, (1993).
Williams, M. *Trends in Biotechnology*, 13: 344–349, (1995).

*Primary Examiner*—David T. Fox
*Attorney, Agent, or Firm*—Foley & Lardner

[57] ABSTRACT

Male-sterile plants can be produced by increasing the endogenous concentration of avidin in the plant tissues. This effect can be achieved by producing transgenic plants containing an expression vector in which a promoter is operably linked to a DNA sequence encoding avidin. Methods for restoring male fertility are disclosed. Additionally, methods for production of seeds with one or more desired grain traits are provided.

42 Claims, 2 Drawing Sheets

INDUCTION OF MALE STERILITY IN PLANTS BY EXPRESSION OF HIGH LEVELS OF AVIDIN

This is a Continuation-In-Part application of application Ser. No. 08/475,582 which was originally filed on Jun. 7, 1995 and is now abandoned.

FIELD OF THE INVENTION

The present invention relates to a method for controlling fertility of plants using DNA molecules that encode avidin. In particular, this invention is directed to methods for producing transgenic, male-sterile plants which express avidin. Moreover, this invention is directed to methods for restoring male fertility in the progeny of male-sterile plants. The invention also relates to methods for production of hybrid seeds, in particular, hybrid seeds with one or more desired grain or seed traits, using male-sterile plants which express avidin.

BACKGROUND OF THE INVENTION

Control of pollen fertility is essential in hybrid crop production. See, for example, J. M. Poehlman, BREEDING FIELD CROPS, 3rd ed. (Van Nostrand and Reinhold, New York, N.Y., 1987), which is herein incorporated by reference. In hybrid maize production, for example, control of pollen fertility is typically accomplished by physically removing the male inflorescence, or tassel, prior to pollen shed. Manual detasseling is highly labor intensive. Although mechanical detasseling is less labor intensive than manual detasseling, it is less reliable and requires subsequent examination of the crop and commonly, remedial manual detasseling. Both methods of detasseling cause a loss of female parent yield.

Most major crop plants of interest, however, have both functional male and female organs within the same flower; therefore, emasculation is not a simple procedure. While it is possible to remove by hand the pollen-forming organs before pollen is shed, this form of hybrid production is extremely labor intensive and expensive.

Pollen fertility also can be controlled by applying a foliar spray having male gametocidal properties. Cross et al., *Sex Plant Reprod.* 4: 235 (1991). For example, the application of ethrel to anthers results in additional pollen mitoses in wheat, degeneration of tapetal cells in barley, and malformed or aborted pollen in Eragrostis. Bennet et al., *Nature* 240: 566 (1972), Colhoun et al., *Plant Cell Environ.* 6: 21 (1983); Berthe et al., *Crop Sci.* 18: 35 (1978). However, the chemical approach is labor intensive, presents potential problems with the toxicity of chemicals introduced into the environment, and can be very sensitive to the timing of application.

In addition, commercial production of hybrid seed by use of gametocides is limited by the expense and availability of the chemicals, as well as by the reliability and length of action of the applications. A serious limitation of gametocides is that they have phytotoxic effects, the severity of which are dependent on genotype. Other limitations include that these chemicals may not be effective for crops with an extended flowering period because new flowers produced may not be affected. Consequently, repeated application of chemicals is required.

Many current commercial hybrid seed production systems for field crops rely on a genetic means of pollination control. Plants that are used as females either fail to shed pollen, produce pollen that is biochemically unable to effect self-fertilization, or fail to make pollen. Plants that are unable to self-fertilize are said to be "self-incompatible." Difficulties associated with the use of a self-incompatibility system include availability and propagation of the self-incompatible female line, and stability of the self-compatibility. In some instances, self-incompatibility can be overcome chemically, or immature buds can be pollinated by hand before the bio-chemical mechanism that blocks pollen is activated. Self-incompatible systems that can be deactivated are often very vulnerable to stressful climatic conditions that break or reduce the effectiveness of the biochemical block to self-pollination.

Of more widespread interest for commercial seed production are genetic pollen-control-based systems causing male sterility. These systems are of two general types: (1) nuclear male sterility, which is the failure of pollen formation because of mutations in one or more nuclear genes or (2) cytoplasmic-genetic male sterility, commonly referred to as "cytoplasmic male sterility" (CMS), in which pollen formation is blocked or aborted because of an alteration in a cytoplasmic organelle, which generally is the mitochondria.

Nuclear sterility can be either dominant or recessive. Typically, dominant sterility can only be used for hybrid seed formation if vegetative or clonal propagation of the female line is possible. Recessive sterility can be used if sterile and fertile plants are easily discriminated. Commercial utility of dominant and recessive sterility systems is limited, however, by the expense of clonal propagation and rouging the female rows of self-fertile plants, respectively.

Although there are hybridization schemes involving the use of CMS, there are limitations to its commercial value. One example of a CMS system is a specific mutation in the cytoplasmically located mitochondria which can, when in the proper nuclear background, lead to the failure of mature pollen formation. In some instances, the nuclear background can compensate for the cytoplasmic mutation and normal pollen formation occurs. Specific nuclear "restorer genes" allow pollen formation in plants with CMS mitochondria. Generally, the use of CMS for commercial seed production involves the use of three breeding lines: a male-sterile line (female parent), a maintainer line which is isogenic to the male-sterile line but contains fully functional mitochondria, and a male parent line. The male parent line may or may not carry the specific restorer genes in the cytoplasm.

For crops such as vegetables for which seed recovery from the hybrid is unimportant, a CMS system can be used without restoration. For crops for which the fruit or seed of the hybrid is the commercial product, the fertility of the hybrid seed must be restored by specific restorer genes in the male parent or the male-sterile hybrid must be pollinated. Pollination of non-restored hybrids can be achieved by including a small percentage of male fertile plants to effect pollination. In most species, the CMS trait is inherited maternally, since all cytoplasmic organelles are usually inherited from the egg cell only.

CMS systems possess limitations that can preclude them as a sole solution to production of male sterile plants. For example, one particular CMS type in maize (T-cytoplasm) confers sensitivity to the toxin produced by infection by a particular fungus. Although still used for a number of crops, CMS systems may break down under certain environmental conditions.

It is apparent therefore that a means to control pollen production by other than manual, mechanical, chemical and traditional genetic methods is greatly to be desired.

SUMMARY OF THE INVENTION

Accordingly, it is an object of the present invention to provide a method to produce male-sterile plants that are rendered sterile by heterologous expression of avidin.

It is a further object of this invention to provide a chimeric gene comprising a DNA sequence that encodes avidin which is operably linked to a plant promoter sequence.

It is a further object of the invention to produce a method of reversing male sterility caused by expression of avidin.

It is another object of the invention to provide methods for production of seeds with one or more desired grain or seed traits.

These and other objects are achieved, in accordance with one embodiment of the present invention, by the provision of an isolated DNA molecule comprising a nucleotide sequence encoding avidin operably linked to a plant promoter sequence. In a preferred embodiment the isolated DNA sequence is contained in an expression vector. In another preferred embodiment the plant promoter sequence is a constitutive promoter, and in another preferred embodiment the constitutive promoter is a ubiquitin promoter. In another preferred embodiment the avidin gene is operably linked to an export signal sequence.

In accordance with another embodiment of the invention there is provided a transgenic plant, in which the plant comprises a heterologous nucleotide sequence comprising an avidin gene, and wherein the heterologous nucleotide sequence increases the concentration of avidin in the tissues of the plant, causing male sterility. In preferred embodiments the transgenic plant is a corn plant, a soybean plant, a canola plant, or a sunflower plant. In another preferred embodiment the heterologous DNA molecule further comprises a constitutive promoter sequence, which in a preferred embodiment is a ubiquitin promoter sequence. In another preferred embodiment the heterologous DNA molecule further comprises a tissue-specific promoter. The particularly preferred tissue-specific promoter is an anther-specific promoter.

In accordance with still another aspect of the invention there is provided a method of producing a transgenic male-sterile plant, comprising introducing into plant cells an expression vector comprising a promoter and an avidin gene, wherein the promoter controls the expression of the avidin gene, and where the avidin gene expression causes male sterility. In a preferred embodiment a transgenic plant is regenerated from the plant cells. In another preferred embodiment the promoter comprises a ubiquitin promoter, a tissue-specific promoter, or an inducible promoter.

In accordance with still another aspect of the invention there is provided a method of using an avidin gene to produce a male-fertile hybrid plant, comprising producing a first parent male-sterile plant comprising a DNA molecule as described above, in which the expression of avidin causes male sterility, producing a second transgenic parent plant expressing a second foreign gene, and cross-fertilizing the first parent with the second parent to produce a hybrid plant that expresses the second foreign gene, and in which the product of the second foreign gene reduces expression of avidin in the hybrid plant, thereby producing a male-fertile hybrid plant.

In a preferred embodiment of this aspect of the invention the second foreign gene is selected from the group consisting of an antisense gene, a ribozyme gene and an external guide sequence gene. In another preferred embodiment the antisense gene comprises avidin mRNA sequences, which in a further preferred embodiment is under the control of an inducible promoter. In still another preferred embodiment the ribozyme gene comprises avidin mRNA sequences. In yet another preferred embodiment the external guide sequence gene comprises avidin mRNA sequences. In still further preferred embodiments the DNA molecule of the first parent plant further comprises a LexA operator which is operatively linked to said promoter, wherein the second foreign gene is the LexA repressor gene. In another preferred embodiment the promoter sequence is an anther-specific promoter sequence comprising an anther box selected from the group consisting of the nucleotide sequence of SEQ ID NO:1; the nucleotide sequence of SEQ ID NO:2; the nucleotide sequence of SEQ ID NO:3; and a functional fragment thereof.

In still another preferred embodiment of this aspect of the invention the anther box has the nucleotide sequence of SEQ ID NO:1, SEQ ID NO:2, or SEQ ID NO:3, and the anther-specific promoter further comprises a core promoter selected from the group consisting of: CaMV 35S core promoter; the nucleotide sequence of SEQ ID NO:4; the nucleotide sequence of SEQ ID NO:5; the nucleotide sequence of SEQ ID NO:6; and functional fragments thereof.

In accordance with a still further aspect of the invention there is provided a method for restoring fertility in a plant rendered male sterile by expression of avidin, comprising spraying the plant with a solution of biotin.

In accordance with yet another aspect of the invention there is provided a method for producing seeds having one or more grain or seed traits of interest. In a preferred embodiment of this invention a first parent plant, which is male sterile and carries one or more copies of the avidin gene, is crossed as the female parent to a second parent plant, which is male fertile and carries one or more grain or seed traits of interest. Seeds are produced with the grain or seed traits of the male parent. In preferred embodiments the parent plant is corn, soybean, canola or sunflower. In yet another preferred embodiment of the invention the avidin gene is the streptavidin gene.

DETAILED DESCRIPTION OF THE PREFERRED EMBODIMENTS

1. Definitions

Figure 1:
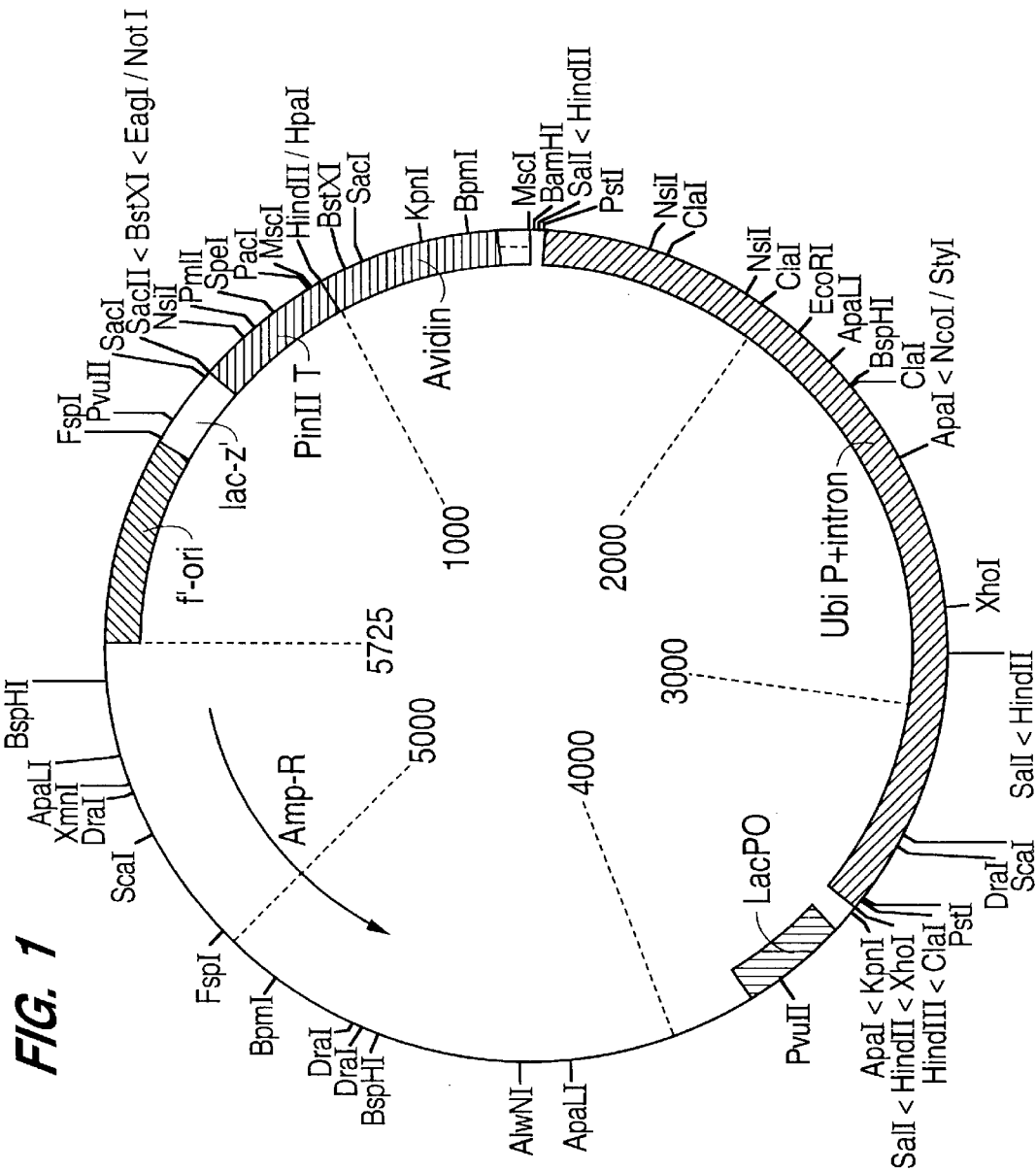
FIG. 1 shows the avidin-encoding plasmid PHI5168 in which a maize ubiquitin promoter (including its first exon plus first intron) drives expression of a barley alpha amylase export signal sequence and an avidin coding region.

In the description that follows, a number of terms are used extensively. The following definitions are provided to facilitate understanding of the invention.

A structural gene is a DNA sequence that is transcribed into messenger RNA (mRNA) which is then translated into a sequence of amino acids characteristic of a specific polypeptide.

A foreign gene refers in the present description to a DNA sequence that is operably linked to at least one heterologous regulatory element. For example, any gene other than the maize 5126 structural gene is considered to be a foreign gene if the expression of that gene is controlled by an anther-specific regulatory element of the 5126 gene.

A promoter is a DNA sequence that directs the transcription of a gene, such as a structural gene, an antisense gene, a ribozyme gene or an external guide sequence gene. Typically, a promoter is located in the 5' region of a gene, proximal to the transcriptional start site. If a promoter is an inducible promoter, then the rate of transcription increases in response to an inducing agent. In contrast, the rate of transcription is not regulated by an inducing agent if the promoter is a constitutive promoter. A plant promoter is a promoter sequence that will direct the transcription of a gene in plant tissue.

A core promoter contains essential nucleotide sequences for promoter function, including the TATA box and start of transcription. By this definition, a core promoter may or may not have detectable activity in the absence of specific sequences that may enhance the activity or confer tissue specific activity. For example, the SGB6 core promoter consists of about 38 nucleotides 5'-ward of the transcriptional start site of the SGB6 gene, while the Cauliflower Mosaic Virus (CaMV) 35S core promoter consists of about 33 nucleotides 5'-ward of the transcriptional start site of the 35S genome.

A tissue-specific promoter is a DNA sequence that, when operably linked to a gene, directs a higher level of transcription of that gene in a specific tissue than in some or all other tissues in an organism. For example, an anther-specific promoter is a DNA sequence that directs a higher level of transcription of an associated gene in plant anther tissue. The SGB6 anther-specific promoter, for example, can direct the expression of a foreign gene in anther tissue, but not in root tissue or coleoptile tissue.

As used herein, an "anther-specific promoter" comprises two functional elements: an "anther box" and a core promoter. A particular anther box may possess the functional characteristics of a classic enhancer. The combination of an anther box and a core promoter can stimulate gene expression to a greater extent than a core promoter alone. This is true even in the case of a chimeric anther-specific promoter containing an anther box and a core promoter derived from different genes. Such chimeric anther-specific regulatory elements are described below.

An operator is a DNA sequence that is located 5'-ward of a gene and that contains a nucleotide sequence which is recognized and bound by a repressor protein. The binding of a repressor protein with its cognate operator results in the inhibition of the transcription of the gene. For example, the LexA gene encodes a repressor protein that binds to the LexA operator.

An isolated DNA molecule is a fragment of DNA that has been separated from the DNA of an organism. For example, a cloned DNA molecule encoding an avidin gene is an isolated DNA molecule. Another example of an isolated DNA molecule is a chemically-synthesized DNA molecule, or enzymatically-produced cDNA, that is not integrated in the genomic DNA of an organism.

An enhancer is a DNA regulatory element that can increase the efficiency of transcription.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term expression refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain a foreign gene.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

A ribozyme is an RNA molecule that contains a catalytic center. The term includes RNA enzymez, self-splicing RNAs, and self-cleaving RNAs. A DNA sequence that encodes a ribozyme is-termed a ribozyme gene.

An external guide sequence is an RNA molecule that directs the endogenous ribozyme, RNase P, to a particular species of intracellular mRNA, resulting in the cleavage of the mRNA by RNase P. A DNA sequence that encodes an external guide sequence is termed an external guide sequence gene.

A grain or seed trait is a nutritional or physiological characteristic of the seed, preferably controlled by a dominant gene, which significantly affects industrial type. The grain or seed traits include such characteristics as oil, protein and starch content, as well as protein quality and starch type.

A single cross is a cross between two inbred lines.

A double cross is a cross between two single crosses.

A three-way cross is the progeny of a cross between a single-cross and an inbred line.

A hybrid is first generation offspring of a cross between two individuals differing in one or more genes.

An inbred line is a pure line usually originating by self-pollination and selection.

A synthetic line is a mixture of strains, clones, inbreds or hybrids among them, maintained by open-pollination for a specified number of generations. The component units are propagated and the synthetic reconstituted at regular intervals.

Specific combining ability is the performance of specific combinations of genetic strains in crosses in relation to the average performance of all combinations.

A pollinator plant is the male fertile parent which donates pollen to the male sterile female parent. A pollinator plant may have any one of many different genetic backgrounds and therefore may be an inbred line, a hybrid, a synthetic open pollinated line or a genetic stock. A pollinator plant may be a transgenic line. A pollinator plant may carry one or more seed or grain traits of interest.

2. Overview

The present invention provides methods for generating male sterile plants by preparing transgenic plants that express avidin. The avidin can be expressed constitutively, in a non-tissue specific manner, or can be expressed in an anther-specific manner. Methods for restoring male fertility are also provided.

Also provided is a method for producing hybrid seeds having one or more grain or seed traits of interest. In a preferred embodiment of this invention a first hybrid, which is male sterile and carries one or more copies of the avidin gene, is crossed as the female parent to a second hybrid, which is male fertile and carries one or more grain or seed traits of interest. Hybrid seeds are produced with one or more grain or seed traits of the male parent.

An avidin gene is isolated and inserted into an expression vector suitable for introduction into plant tissue. The expression vector further comprises a promoter which may be a constitutive promoter, a non-tissue specific promoter, such as the ubiquitin promoter, a tissue specific promoter such as an anther-specific promoter, or an inducible promoter. The expression vector may comprise an export signal sequence. High level expression of a gene product which then accumulates in the cytoplasm may result in toxicity to the plant cell. Removal of the gene product from the cytoplasm thus may result in reduced cell toxicity. Plant genes and their export signal sequences are known. See Jones and Robinson, Tansley Review 17: 567–597 (1989). The expression vector is introduced into plant tissue by standard methods and transgenic plants are selected and propagated. The transgenic plants that express avidin are male sterile. Male fertility can be restored by coexpression in the transgenic plants of a second gene that inhibits transcription of the avidin gene, or inhibits translation of avidin mRNA. According to this embodiment, temporary suppression of the avidin gene is achieved if the suppressor gene is operably linked to an inducible promoter. Alternatively, male fertility can be restored by spraying developing plants with solutions of biotin.

3. Isolation of DNA Molecules that Encode Avidin

Nucleotide sequences encoding avidin can be isolated by known methods. For example, the nucleotide sequence of the streptavidin gene is known. Argarana et al., *Nucleic Acids Res.*, 14(4): 1871–1882 (1986). Alternatively, a cDNA encoding chicken egg white avidin can be isolated from a chicken oviduct cDNA library by the methods described by Gope et al., *Nucleic Acids Res.*, 15: 3595 (1987), which is incorporated herein by reference.

Genomic clones of the avidin gene can be obtained from genomic DNA of organisms that are known to produce avidin. For example, a chicken avidin gene can be cloned from chicken genomic DNA by the methods described in Keinanen et al., *Eur. J. Biochem.* 220: 615 (1994).

Avidin genes can also be isolated using the polymerase chain reaction (PCR) using standard methods. See Erlich, PCR TECHNOLOGY: PRINCIPLES AND APPLICATIONS FOR DNA AMPLIFICATION (Stockton Press, NY, 1989) and Innis et al., PCR PROTOCOLS: A GUIDE TO METHODS AND APPLICATIONS (Academic Press, San Diego, 1990). Methods for PCR amplification of long nucleotide sequences, such as the ELONGASE™ system (Life Technologies, Inc., Gaithersburg, Md.) can also be used for obtaining longer nucleotide sequences, such as genomic clones encoding avidin. PCR primers complementary to the 5' and 3' termini of known avidin gene sequences can be synthesized using commercial oligonucleotide synthesizers, such as those supplied by Applied Biosystems (Foster City, Calif.). In a preferred embodiment, the primers include additional nucleotide sequences containing restriction endonuclease cleavage sites. The presence of such sites allows for the directional cloning of PCR products into suitable cloning vectors after treatment with an appropriate restriction enzyme. See Finney, "Molecular Cloning of PCR Products" in CURRENT PROTOCOLS IN MOLECULAR BIOLOGY, Ausubel et al. Eds. (John Wiley & Sons, New York, 1987) p. 15.7.1.

Template DNA for the PCR can either be cDNA or genomic DNA, and can be prepared from an appropriate organism using methods well known in the art. Sambrook et al., MOLECULAR CLONING: A LABORATORY MANUAL, Second Edition, (Cold Spring Harbor Laboratory Press, Cold Spring Harbor, N.Y. 1989). Genomic DNA can be directly prepared from avian, reptilian, or amphibian tissue using commercials reagents, such as Triazol™ (Life Technologies, Inc., Gaithersburg, Md.). Alternatively, cDNA encoding avidin can be prepared using mRNA extracted from chicken oviduct tissue using a commercially available kit (Pharmacia, Piscataway, N.J.). The mRNA preparation is used as a template for cDNA synthesis using poly(dT) or random hexamer primers by standard techniques. See Sambrook et al., supra. cDNA synthesis is then carried out using a commercially available kit (Pharmacia), and the cDNA used directly for PCR using the method of Saiki et al., *Science* 239: 487 (1988).

Genomic DNA or cDNA fragments isolated by the methods described above can be inserted into a vector, such as a bacteriophage or cosmid vector, in accordance with conventional techniques, such as the use of restriction enzyme digestion to provide appropriate termini, the use of alkaline phosphatase treatment to avoid undesirable joining of DNA molecules, and ligation with appropriate ligases. Techniques for manipulation of such vectors are disclosed by Ausubel et al. (eds.), CURRENT PROTOCOLS IN MOLECULAR BIOLOGY, pages 3.0.5–3.17.5 (1990) ["Ausubel"].

Alternatively, nucleotide sequences encoding avidin can be obtained by synthesizing DNA molecules encoding avidin using mutually priming long oligonucleotides. See, for example, Ausubel at pages 8.2.8 to 8.2.13. Also, see Wosnick et al., *Gene* 60: 115 (1987). Current techniques using the polymerase chain reaction provide the ability to synthesize genes as large as 1.8 kilobases in length. Adang et al., *Plant Molec. Biol.* 21: 1131 (1993); Bambot et al., *PCR Methods and Applications* 2: 266 (1993). The nucleotide sequence of a synthesized avidin gene can be based upon any known avidin-encoding DNA molecule. See, for example, Gope et al., supra.

These clones can be analyzed using a variety of standard techniques such as restriction analysis, Southern analysis, primer extension analysis, and DNA sequence analysis. Primer extension analysis or S1 nuclease protection analysis, for example, can be used to localize the putative start site of transcription of the cloned gene. Ausubel at pages 4.8.1–4.8.5; Walmsley et al., "Quantitative and Qualitative Analysis of Exogenous Gene Expression by the S1 Nuclease Protection Assay," in METHODS IN MOLECULAR BIOLOGY, VOL. 7: GENE TRANSFER AND EXPRESSION PROTOCOLS, Murray (ed.), pages 271–281 (Humana Press Inc. 1991). These and related techniques well known to one skilled in the art are employed for isolation of other genes of interest, and their cloning and expression.

4. Cloning of an Avidin Gene into an Expression Vector and Preparation of Transgenic Plants Once an avidin gene has been isolated it is placed into an expression vector by standard methods. See Sambrook et al., supra. The selection of an appropriate expression vector will depend upon the method of introducing the expression vector into host cells. Typically, an expression vector contains: (1) prokaryotic DNA elements coding for a bacterial replication origin and an antibiotic resistance gene to provide for the growth and selection of the expression vector in the bacterial host; (2) a cloning site for insertion of an exogenous DNA sequence, for example an avidin gene; (3) eukaryotic DNA elements that control initiation of transcription of the exogenous gene, such as a promoter; (4) DNA elements that control the processing of transcripts, such as a transcription termination/polyadenylation sequence; and (5) a gene encoding a marker protein (e.g., a reporter gene), wherein the gene is operably linked to the DNA elements that control transcription initiation. Additionally, the expression vector may comprise a DNA sequence encoding a export signal sequence operably linked to the exogenous DNA sequence. General descriptions of plant expression vectors and reporter genes can be found in Gruber et al., "Vectors for Plant Transformation," in METHODS IN PLANT MOLECULAR BIOLOGY AND BIOTECHNOLOGY, Glick et al. (eds.), pages 89–119 (CRC Press, 1993).

In a preferred embodiment of the present invention a plant ubiquitin promoter system is used. Plant ubiquitin promoters are well known in the art. See, for example, European Patent Application 0 342 926, which is incorporated herein by reference. The ubiquitin promoter is a constitutive promoter.

In another preferred embodiment of the invention, an inducible promoter is used to allow inducible regulation of the expression of avidin. An example of such an inducible promoter is the glutathione S-transferase system in maize. See Wiegand et al., Plant Mol. Biol. 7: 235 (1986). This method also allows for reversible induction of male sterility. Thus, expression of avidin and concomitant male sterility, can be controlled as desired by activation of the promoter. When the promoter is not activated, avidin is not expressed, and the plants are male fertile.

The expression may comprise a selectable or screenable marker. Many of the commonly used positive selectable marker genes for plant transformation were isolated from bacteria and code for enzymes that metabolically detoxify a selective chemical agent which may be an antibiotic or a herbicide. Other positive selective marker genes encode an altered target which is insensitive to the inhibitor.

A commonly used selectable marker gene for plant transformation is the neomycin phosphotransferase II (nptII) gene, isolated from Tn5, which when placed under the control of plant regulatory signals confers resistance to kanamycin. Fraley et al., Proc. Natl Acad. Sci. U.S.A. 80: 4803 (1983). Another commonly used selectable marker is the hygromycin phosphotransferase gene which confers resistance to the antibiotic hygromycin. Vanden Elzen et al., Plant Mol. Biol. 5: 299 (1985). Additional positive selectable marker genes of bacterial origin that confer resistance to antibiotics include gentamycin acetyl transferase, streptomycin phosphotransferase, aminoglycoside-3'-adenyl transferase and the bleomycin resistance determinant. Hayford et al., Plant Physiol. 86: 1216 (1988); Jones et al., Mol. Gen. Genet. 210: 86 (1987); Svab et al., Plant Mol. Biol. 14: 197 (1990), Hille et al., Plant Mol. Biol. 7: 171 (1986).

Other positive selectable marker genes for plant transformation are not of bacterial origin. These genes include mouse dihydrofolate reductase, plant 5-enolpyruvylshikimate-3-phosphate synthase and plant acetolactate synthase. Eichholz et al., Somatic Cell Mol. Genet. 13: 67 (1987); Shah et al., Science 233: 478 (1986); Charest et al., Plant Cell Rep. 8: 643 (1990).

Other common selectable marker genes for plants confer resistance to herbicidal inhibitors of glutamine synthetase. European Patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., Bio/Technology 7: 61 (1989), describe the production of transgenic plants that express chimeric bar genes coding for phosphinothricin-acetyl-transferase activity.

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression.

Commonly used genes for screening presumptively transformed cells include β-glucuronidase (GUS), β-galactosidase, luciferase and chloramphenicol acetyltransferase. Jefferson, Plant Mol. Biol. Rep. 5: 387 (1987); Teeri et al., EMBO J. 8: 343 (1989); Koncz et al., Proc. Natl Acad. Sci. U.S.A. 84: 131 (1987); De Block et al., EMBO J. 3: 1681 (1984). Another approach to the identification of relatively rare transformation events has been use of a gene that encodes a dominant constitutive regulator of the Zea mays anthocyanin pigmentation pathway. Ludwig et al., Science 247: 449 (1990).

The expression vectors may comprise the avidin gene operably linked to a DNA sequence that codes for a peptide export signal sequence. See Hones and Robinson, supra. The vector is made such that a signal sequence is fused to the N-terminal of the mature avidin protein sequence, allowing for normal cellular processing to cleave accurately the protein molecule and yield mature active avidin. In a particularly preferred embodiment, signal sequence is the barley alpha amylase signal sequence. Rogers, J. Biol. Chem. 260: 3731–3738 (1985).

Expression vectors containing an avidin gene can be introduced into protoplasts, or into intact tissues, such as immature embryos and meristems, or into callus cultures, or into isolated cells. Preferably, expression vectors are introduced into intact tissues. General methods of culturing plant tissues are provided, for example, by Miki et al., "Procedures for Introducing Foreign DNA into Plants," in METHODS IN PLANT MOLECULAR BIOLOGY AND BIOTECHNOLOGY, Glick et al. (eds.), pages 67–88 (CRC Press, 1993), and by Phillips et al., "Cell/Tissue Culture and In Vitro Manipulation," in CORN AND CORN IMPROVEMENT, 3rd Edition, Sprague et al. (eds.), pages 345–387 (American Society of Agronomy, Inc. et al. 1988).

Methods of introducing expression vectors into plant tissue include the direct infection or co-cultivation of plant tissue with *Agrobacterium tumefaciens*. Horsch et al., *Science* 227: 1229 (1985). Preferably, a disarmed Ti-plasmid is used as a vector for foreign DNA sequences. Transformation can be performed using procedures described, for example, in European patent application Nos. 116 718 (1984) and 270 822 (1988). Preferred Ti-plasmid vectors contain the foreign DNA sequence between the border sequences, or at least located upstream of the right border sequence.

Other types of vectors can be used for transforming plant cells using procedures such as direct gene transfer (see, for example, PCT application WO 85/01856 and European application 275 069), in vitro protoplast transformation (for example, U.S. Pat. No. 4,684,611), plant virus-mediated transformation (for example, European application No. 067 553 and U.S. Pat. No. 4,407,956), and liposome-mediated transformation (for example, U.S. Pat. No. 4,536,475). Suitable methods for corn transformation are provided by Fromm et al., *Bio/Technology* 8: 833 (1990), and by Gordon-Kamm et al., *The Plant Cell* 2: 603 (1990). Standard methods for the transformation of rice are described by Christou et al., *Trends in Biotechnology* 10: 239 (1992), and by Lee et al., *Proc. Nat'l Acad. Sci. USA* 88: 6389 (1991). Wheat can be transformed using methods that are similar to the techniques for transforming corn or rice. Furthermore, Casas et al., *Proc. Nat'l Acad. Sci. USA* 90: 11212 (1993), describe a method for transforming sorghum, while Wan et al., *Plant Physiol.* 104: 37 (1994), describe a method for transforming barley.

In general, direct transfer methods are preferred for the transformation of a monocotyledonous plant, particularly a cereal such as rice, corn, sorghum, barley or wheat. Suitable direct transfer methods include microprojectile-mediated delivery, DNA injection, electroporation, and the like. See, for example, Gruber et al., supra, Miki et al., supra, and Klein et al., *Bio/Technology* 10: 268 (1992). More preferably, expression vectors are introduced into tissues of a monocotyledonous plant using microprojectile-mediated delivery with a biolistic device.

5. Regulation of Male Fertility
A. Production of Male-Sterile Plants

To induce male sterility pursuant to the present invention, an expression vector is constructed in which a DNA sequence encoding avidin is operably linked to DNA sequences that regulate gene transcription in plant tissue. The general requirements of an expression vector are described above. In order to achieve male sterility by expression of avidin it is preferred that avidin be not merely expressed in a transient manner, but that the expression vector is introduced into plant embryonic tissue in such a manner that avidin will be expressed at a later stage of development in the adult plant. For example, mitotic stability can be achieved using plant viral vectors that provide epichromosomal replication.

A preferred method of obtaining mitotic stability is provided by the integration of expression vector sequences into the host chromosome. Such mitotic stability can be provided by the microprojectile delivery of an expression vector to plant tissue, or by using other standard methods as described above. See, for example, Fromm et al., *Bio/Technology* 8: 833 (1990), Gordon-Kamm et al., *The Plant Cell* 2: 603 (1990), and Walters et al., *Plant Molec. Biol.* 18: 189 (1992).

Transcription of the avidin gene after introduction into plant tissue is preferably controlled by a constitutive promoter that non-specifically stimulates gene expression in plant tissue. An example of a constitutive promoter suitable for this purpose is the ubiquitin promoter, as described supra.

Transcription of the avidin gene may also be controlled by a promoter which stimulates gene expression in a tissue-specific manner. A particularly preferred anther-specific promoter is the 5126 promoter which was isolated from the maize inbred B73 line. The 5126 promoter stimulates the expression of a foreign gene from quartet to early uninucleate microspore-stage anthers.

Another suitable anther-specific promoter is the SGB6 promoter, which also was isolated from the B73 line. The SGB6 promoter can induce expression of a foreign gene in anther tapetal cells from the quartet stage to the mid-uninucleate stage of microspore development.

Alternatively, anther-specific gene expression can be provided using a combination of an anther box and a core promoter. A particularly preferred anther box is a 5126 anther box which comprises the following nucleotide sequence:

```
                                              [SEQ ID NO:1]
5' GCGGCCGCGG ATCCGCTCAT CTGCTCGGTA CCAACCAGCC

CGCCGGCGCC TAGGCGAGTA GACGAGCCAT GGTTGGTCGG

TTTCCTATTA CCATGCACAG ATCT 3'

AAAGGATAAT GGTACGTGTC TAGA
```

Another suitable anther box resides within a 94 base pair DNA fragment defined by nucleotides 583 to 490 upstream of the SGB6 start site of transcription. The nucleotide sequence of the 94 base pair SGB6 anther box is:

```
                                              [SEQ ID NO:2]
(-583) ACAGTTCACT AGATATGCAT GATCTTTAAC AATTGCTGCT

TGTCAAGTGA TCTATACGTA CTAGAAATTG TTAACGACGA

GGATTGTGCG GTTTCTTTTG GCACAAATGG CATGAACAGA

CCTAACACGC CAAAGAAAAC CGTGTTTACC GTACTTGTCT

GTAATCCGGG ACGC (-490)

CATTAGGCCC TGCG.
```

Alternatively, a suitable anther box is obtained from the maize G9 promoter, which stimulates gene expression during the meiotic to quartet stages of development. The G9 anther box comprises the following nucleotide sequence:

```
                                              [SEQ ID NO:3]
5' GCGGCCGCGG ATCCTGGCTG GATGAAACCG ATGCGAGAGA.

CGCCGGCGCC TAGGACCGAC CTACTTTGGC TACGCTCTCT

AGAAAAAAAA ATTGTTGCAT GTAGTTGGCG CCTGTCACCC

TCTTTTTTTT TAACAACGTA CATCAACCGC GGACAGTGGG

AACCAAACCA GTAGTTGAGG CACGCCCTGT TTGCTCACGA

TTGGTTTGGT CATCAACTCC GTGCGGGACA AACGAGTGCT

TCACGAACGT AGATCT 3'

AGTGCTTGCA TCTAGA
```

The 5126, SGB6 and G9 anther boxes can be obtained by synthesizing oligonucleotides, as described above. Those of skill in the art will appreciate that deletion analysis can be performed to localize one or more additional anther-specific regulatory sequences within the disclosed anther boxes. Such "functional fragments" of the anther boxes also can be used to regulate avidin gene expression in an anther-specific manner.

Preferred core promoters are derived from the 5126 core promoter, the SGB6 core promoter, the G9 core promoter and the Cauliflower Mosaic Virus 35S core promoter.

A particularly preferred core promoter is the 5126 core promoter which comprises the following nucleotide sequence:

[SEQ ID NO:4]
```
5' AGATCTAAGT AAGGTATATA TGTGCATAGT CTCCTAATTC

TCTAGATTCA TTCCATATAT ACACGTATCA GAGGATTAAG

TTCATCTTCA ACCTCTAGCT GATTGATCTC TGGTATTTAC

AAGTAGAAGT TGGAGATCGA CTAACTAGAG ACCATAAATG

CACTCTTTCC TTCCTTCCTT CCTTCAATTC TAAATACCAC

GTGAGAAAGG AAGGAAGGAA GGAAGTTAAG ATTTATGGTG

AAATCAAAGT TGCTTTGCCA TG 3'

TTTAGTTTCA ACGAAACGGT AC.
```

The SGB6 core promoter consists of about 38 nucleotides upstream of the transcriptional start site of the SGB6 gene. A suitable SGB6 core promoter has the following nucleotide sequence:

[SEQ ID NO:5]
```
5' ATCTCACCCT ATTAATACCA TGCTGACGAG

TAGAGTGGGA TAATTATGGT ACGACTGCTC

CCAATAGC 3'

GGTTATCG.
```

A suitable core promoter derived from the G9 gene comprises the nucleotide sequence:

[SEQ ID NO:6]
```
5' AGATCTCTAT AAAACACGCA GGGACTGGAA AGCGAGATTT

TCTAGAGATA TTTTGTGCGT CCCTGACCTT TCGCTCTAAA

CACAGCTGAA AGCAGCCAAA ACGCAGAAGC TGCACTGCAT

GTGTCGACTT TCGTCGGTTT TGCGTCTTCG ACGTGACGTA

ACATCGAGCT AACTATCTGC AGCCATG 3'

TGTAGCTCGA TTGATAGACG TCGGTAC.
```

Suitable core promoters also are provided by functional fragments of 5126, SGB6 and G9 core promoters. Methods for obtaining such functional fragments are described above.

The developmental window of avidin gene expression can be extended by using a chimeric regulatory element comprising an anther box from one gene and an anther-specific promoter from a second gene. For example, SGB6 regulatory sequences stimulate gene expression from quartet through mid-uninucleate stages of development, while G9 regulatory sequences stimulate gene expression during meiosis and through the quartet stage of development. Yet the combination of an SGB6 anther box and a G9 promoter stimulates transcription of a foreign gene during meiosis and through the mid-uninucleate stage of development. Thus, various combinations of anther boxes and anther-specific promoters are particularly useful for the present invention.

A viral core promoter also may be used. Examples of suitable viral core promoters include a Cauliflower Mosaic Virus (CaMV) core promoter, a Figwort Mosaic Virus core promoter, and the like. Gruber et al., supra. Preferably, the viral core promoter is the CaMV 35S core promoter, or a variant thereof.

In order to select transformed cells, the expression vector contains a selectable marker gene, such as a herbicide resistance gene. For example, such genes may confer resistance to phosphinothricine, glyphosate, sulfonylureas, atrazine, or imidazolinone. Preferably, the selectable marker gene is the bar gene or pat gene which encodes phosphinothricin acetyltransferase. The nucleotide sequences of bar genes can be found in Leemans et al., European patent application No. 0-242-246 (1987), and in White et al., *Nucleic Acids Res.* 18: 1062 (1990). Wohlleben et al., *Gene* 70: 25 (1988), disclose the nucleotide sequence of the pat gene. Bar or pat gene expression confers resistance to herbicides such as glufosinate (sold as Basta® and Ignite®, among others) and bialaphos (sold as Herbi-ace® and Liberty®).

The expression vector can contain DNA sequences encoding avidin under the control of a constitutive promoter or an anther-specific promoter, as well as the selectable marker gene under control of a constitutive promoter. Alternatively, the selectable marker gene can be delivered to host cells in a separate selection expression vector by "co-transformation" of embryonic tissue.

B. Restoration of Male Fertility in the F1 Hybrid

The above-described methods can be used to produce transgenic male-sterile plants for the production of F1 hybrids in large-scale directed crosses between inbred lines. If all egg cells of the transgenic male-sterile plants do not contain the recombinant avidin gene, then a proportion of F1 hybrids will have a male-fertile phenotype. On the other hand, F1 hybrids will have a male-sterile phenotype if the recombinant avidin gene is present in all egg cells of the transgenic male-sterile plants. Thus, it might be desirable to use a male fertility restoration system to provide for the production of male-fertile F1 hybrids. Such a fertility restoration system has particular value in autogamous species when the harvested product is seed.

The commonly proposed approach to restoring fertility in a line of transgenic male-sterile plants requires the production of a second "restorer" line of transgenic plants. For example, a transgenic plant that is male-sterile due to barnase expression would be crossed with a male-fertile plant that expresses the barnase inhibitor, as discussed above. Mariani et al., *Nature* 357: 384 (1992).

In the present case, an analogous approach would require the production of a restorer line of transgenic plants that express ribozymes targeted to avidin mRNA or that express antisense avidin. For example, ribozymes can be designed to express endonuclease activity that is directed to a certain target sequence in a mRNA molecule. For example, Steinecke et al., *EMBO J.* 11: 1525 (1992), achieved up to 100% inhibition of neomycin phosphotransferase gene expression by ribozymes in tobacco protoplasts. More recently, Perriman et al., *Antisense Res. & Devel.* 3: 253 (1993), inhibited chloramphenicol acetyl transferase activity in tobacco protoplasts using a vector that expressed a modified hammerhead ribozyme. In the context of the present invention, avidin mRNA provides the appropriate target RNA molecule for ribozymes.

In a similar approach, fertility can be restored by the use of an expression vector containing a nucleotide sequence that encodes an antisense RNA. The binding of antisense RNA molecules to target mRNA molecules results in hybridization arrest of translation. Paterson, et al., *Proc. Natl. Acad. Sci. USA* 74: 4370 (1987). In the context of the present invention, a suitable antisense RNA molecule would have a sequence that is complementary to avidin mRNA. In a preferred embodiment of the invention, the antisense RNA is under the control of an inducible promoter. Activation of this promoter then allows restoration of male fertility.

In a further alternative approach, expression vectors can be constructed in which an expression vector encodes RNA transcripts capable of promoting RNase P-mediated cleavage of avidin mRNA molecules. According to this approach, an external guide sequence can be constructed for directing the endogenous ribozyme, RNase P, to avidin mRNA, which is subsequently cleaved by the cellular ribozyme. Altman et al., U.S. Pat. No. 5,168,053; Yuan et al., Science 263: 1269 (1994). Preferably, the external guide sequence comprises a ten to fifteen nucleotide sequence complementary to avidin mRNA, and a 3'-NCCA nucleotide sequence, wherein N is preferably a purine. Id. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region. Id.

In an alternative method for restoring male fertility, transgenic male-sterile plants contain an expression vector that, in addition to a promoter sequence operably linked to an avidin gene, also contains a prokaryotic regulatory element. Transgenic male-fertile plants are produced that express a prokaryotic polypeptide under the control of the promoter. In the F1 hybrids, the prokaryotic polypeptide binds to the prokaryotic regulatory sequence and represses the expression of avidin.

For example, the LexA gene/LexA operator system can be used to regulate gene expression pursuant to the present invention. See U.S. Pat. No. 4,833,080 ("the '080 patent) and Wang et al., Mol. Cell. Biol. 13: 1805 (1993). More specifically, the expression vector of the male-sterile plant would contain the LexA operator sequence, while the expression vector of the male-fertile plant would contain the coding sequences of the LexA repressor. In the F1 hybrid, the LexA repressor would bind to the LexA operator sequence and inhibit transcription of the avidin gene.

LexA operator DNA molecules can be obtained, for example, by synthesizing DNA fragments that contain the well-known LexA operator sequence. See, for example, the '080 patent and Garriga et al., Mol. Gen. Genet. 236: 125 (1992). The LexA gene may be obtained by synthesizing a DNA molecule encoding the LexA repressor. Gene synthesis techniques are discussed above and LexA gene sequences are described, for example, by Garriga et al., supra. Alternatively, DNA molecules encoding the LexA repressor may be obtained from plasmid pRB500, American Type Culture Collection accession No. 67758.

Those of skill in the art can readily devise other male fertility restoration strategies using prokaryotic regulatory systems, such as the lac repressor/lac operon system or the trp repressor/trp operon system.

Still another method for restoring fertility utilizes the high affinity of avidin for biotin, by spraying developing plants with a solution of biotin. The biotin solution may comprise a minimum amount of an organic co-solvent such as DMSO to ensure complete solubility of the biotin. However, the biotin solution may contain no organic co-solvent. Spraying may commence as early as the meiotic phase of pollen development. Spraying may commence later in pollen development as well. Spraying is generally repeated at regular intervals until pollen shed is observed. The intervals between spraying will vary between 1 and 7 days. In a preferred embodiment of the invention, spraying is repeated every 3 to 5 days.

6. Production of Hybrid Seeds with Desired Grain Traits

Hybrid seeds with one or more desired grain or seed traits can be advantageously produced using the male sterile plant lines of the instant invention. A transgenic line carrying the avidin gene is crossed as the male sterile female parent to a male fertile pollinator plant which carries one or more genes for a desired grain or seed trait. The male fertile pollinator plant line preferably is homozygous for the gene(s) controlling the desired grain or seed trait. Hybrid seeds having the desired grain or seed trait produced by means of this method and are harvested. The method for production of hybrid seeds in which a male sterile parent is crossed to a male fertile pollinator line carrying one or more genes for a desired grain or seed trait is sometimes referred to as the top cross method. See, for example, U.S. Pat. No. 5,196,636, which is incorporated herein by reference.

The male sterile and male fertile lines crossed to make the hybrid seeds of the instant invention can be any compatible combination of hybrid, inbred or synthetic lines. A transgenic line carrying the avidin gene operably linked to a constitutive or inducible promoter is produced using the methods described above. The male sterile line may carry one or more copies of the avidin gene.

A transgenic male sterile line which carries the avidin gene can be selfed by suppressing male sterility by any one of the methods described above. For example, ribozymes can be designed to express endonuclease activity that is directed to a certain target sequence in the avidin mRNA molecule. The gene encoding the ribozyme is operably linked to an inducible promoter. The male sterile plant is treated with the inducer, the ribozyme is expressed, and the avidin mRNA inactivated leading to restoration of male fertility. Alternatively, fertility is restored by the use a nucleotide sequence that encodes an antisense RNA. The binding of antisense RNA molecules to target mRNA molecules results in hybridization arrest of translation. In the context of the present invention, a suitable antisense RNA molecule would have a sequence that is complementary to avidin mRNA. In a preferred embodiment of the invention, the antisense RNA is under the control of an inducible promoter. Activation of this promoter then allows restoration of male fertility.

In a further alternative approach, RNA transcripts capable of promoting RNase P-mediated cleavage of avidin mRNA molecules are produced in the male sterile line. According to this approach, an external guide sequence can be constructed for directing the endogenous ribozyme, RNase P, to avidin mRNA, which is subsequently cleaved by the cellular ribozyme. The external guide sequence transcripts bind to the targeted mRNA species by the formation of base pairs between the mRNA and the complementary external guide sequences, thus promoting cleavage of mRNA by RNase P at the nucleotide located at the 5'-side of the base-paired region.

In yet another approach to restoring male fertility, transgenic male-sterile plant lines are produced which contain an expression vector that, in addition to a promoter sequence operably linked to an avidin gene, also contains a prokaryotic regulatory element. Transgenic lines are produced that contain this avidin gene together with a gene encoding a prokaryotic gene operably linked to an inducible promoter. The transgenic plant line is treated with inducer to produce the prokaryotic polypeptide which binds to the prokaryotic regulatory sequence, represses the expression of avidin and restores male fertility.

Still another method for restoring fertility utilizes the high affinity of avidin for biotin. Transgenic male sterile lines are sprayed with a solution of biotin. The biotin binds to avidin and inactivates it thereby restoring male fertility. The transgenic male sterile lines are generally sprayed with biotin just as the meiotic phase of pollen development commences although biotin spraying may commence later. In a preferred embodiment, suppression of male sterility is achieved by spraying the plant with biotin.

The male sterile and male fertile pollinator lines utilized for production.hybrid seeds with a desired grain or seed trait, according to the methods of the instant invention, are inbred lines, hybrid lines, synthetic open pollinated lines or genetic stock. The inbred lines, hybrid lines, synthetic open pollinated lines or genetic stock are produced by any of the methods well known to the skilled plant breeder. See, for example, J. M. Poehlman, BREEDING FIELD CROPS, 3rd ed. (Van Nostrand and Reinhold, New York, N.Y., 1987), which is herein incorporated by reference. Test crosses among selected inbred and/or hybrid lines are made to evaluate specific combining ability. Commercially acceptable combinations are identified.

A male fertile pollinator plant line is selected which (1) carries one or more genes for a desired grain or seed trait and (2) is compatible with the male sterile line to which it will be crossed. The gene(s) controlling the selected grain trait or seed trait may be dominant so that the trait is readily expressed in the hybrid seeds. However, the gene(s) controlling the selected grain trait or seed trait may be recessive. In the event the gene controlling the grain or seed trait is recessive, the male sterile line and the male fertile pollinator line are each bred to carry this recessive. In the event the gene(s) controlling the grain or seed trait of interest is recessive, both the male sterile and pollinator are preferably homozygous for the gene(s) so that the desired phenotype is expressed in all seed produced by the cross. Accordingly, the male sterile and male fertile pollinator lines may each carry genes which control a grain or seed trait in progeny seeds. The gene(s) for the desired grain or seed trait are introduced into the male sterile line or the male fertile pollinator line by traditionally breeding methods and/or genetic engineering techniques.

The desired grain or seed trait is a nutritional or physiological characteristic of the seed which significantly affects industrial type, germination or disease resistance. The desired grain or seed trait includes such characteristics as oil, protein and starch content, as well as protein quality and starch type. The methods of the instant invention are used to produce specialized seed or grain types which are used in different markets. High oil corn, for example, is used to replace animal fats added to livestock feed. High amylose corn is used to make adhesives, degradable plastic films and packaging material. Starch from waxy corn is used in many different foods such as soups and puddings.

The male fertile pollinator line may carry one or more genes that affect starch and protein characteristics. Genes which affect starch and protein characteristics include, but are not limited to, sugary (su), amylose-extender (ae), brittle (bt), dull (du), floury (fl), opaque (o), horny (h), shrunken (sh) and waxy (wx). See, for example, Hannah et al., *Sci. Hortic.* 55: 177–197 (1993). The properties of starch obtained from maize plants homozygous recessive for ae, du, wx, ae and aewx have been characterized. See Brockett et al., *Starch/Starke* 40: 175–177 (1988) and U.S. Pat. No. 5,516,939.

Alternatively, the pollinator line may be transformed with a gene that affects starch content. For example, the male fertile pollinator may be transformed with a bacterial gene encoding ADPglucose pyrophosphorylase which is active in the presence of metabolites which inhibit the plant enzyme. The resulting seed has a higher starch content. See Sivak et al., *J. of Environ. Polymer Degradation* 3(3): 145–152 (1995).

The pollinator line may carry one or more genes that affect fatty acid content. For example, the fan1 gene controls low linolenic fatty acid in soybean. Hammond et al., *Crop Sci.* 231:192 (1993). The fas$^a$ gene controls high stearic fatty acid content in soybean. Graef et al., *Crop Sci.* 25: 1076 (1985). The fap1 and fap2 genes control low palmitic acid content and high palmitic acid content, respectively, in soybean. Erickson et al., *Crop Sci.* 18: 644 (1988).

The pollinator line may be transformed with a gene which affects seed oil content. For example, the pollinator line may carry a gene encoding stearoyl-acyl carrier protein (stearoyl-ACP) desaturase which catalyzes the first desaturation step in seed oil biosynthesis. The stearoyl-ACP desaturase gene may be operably linked to a seed-specific promoter. Plants such as sunflower, maize, canola or soybean transformed with the stearoyl-ACP desaturase gene produce altered stearic acid levels and can be used to produce seed oil containing modified or altered levels of saturated and unsaturated fatty acids. See, for example, U.S. Pat. No. 5,443,974.

Alternatively, the pollinator line may carry an antisense gene which inhibits the expression of a target gene in the biosynthetic pathway of the grain or seed trait. For example, the pollinator line carries an anitsense gene that inhibits the expression of stearoyl-acyl desaturase. The antisense gene may be operably linked to a seed-specific promoter. Plants transformed with the stearoyl-ACP desaturase antisense gene produce increased stearate levels in seeds. See, for example, Knutzon et al., *Proc. Natl. Acad. Sci. USA* 89: 2624–2628 (1992).

The ratio of male sterile to male fertile pollinator parent seeds planted in the seed production field according to the Top Cross method depends on the genetics of each parent and is varied in order optimize yield. The ratio of male sterile to male fertile pollinator parent ranges from approximately 6:1 to approximately 9:1. Preferably, the ratio of male sterile to male fertile pollinator parent is approximately 8:1. Most preferably, the ratio of male sterile to male fertile pollinator parent is approximately 9:1.

The present invention, thus generally described, will be understood more readily by reference to the following examples, which are provided by way of illustration and are not intended to be limiting of the present invention.

EXAMPLE 1

Preparation of Male Sterile Transgenic Corn by High Constitutive Expression of Avidin A method for formation of transgenic corn plants has been described in European Patent Application No. 0 442 174A1 which is hereby incorporated by reference. A brief description of that methodology follows.

Figure 2:
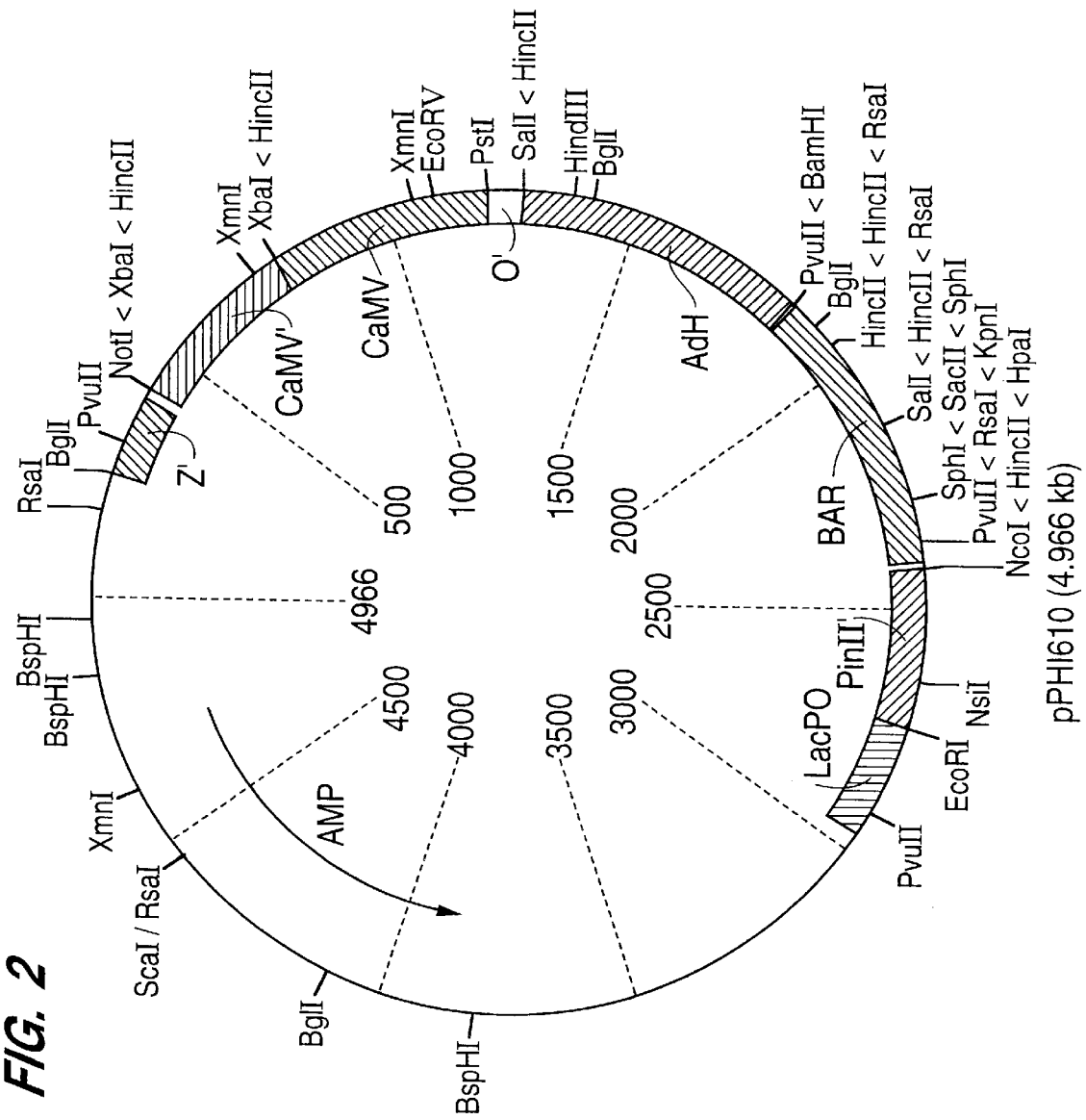
FIG. 2 shows the plasmid PHI610 encoding the bar gene.

PHI5168, a vector carrying the avidin gene under control of the ubiquitin promoter and also containing a PINII terminator sequence, was used to form transgenic corn plants. Plasmid PHI5168 has been deposited with the American Type Culture Collection, 10801 University Blvd., Manassas, Va. on Jan. 21, 1999 and accorded ATCC Accession Number 203604. The structure of PHI5168 is shown in FIG. 1. PHI610, an expression vector carrying the bar gene under control of the double 35S promoter, and also carrying a PINII terminator sequence, was cotransformed along with the avidin construct, allowing the selection of transgenic plants by treatment of the transformation mixture with bialophos. The structure of PHI610 is shown in FIG. 2. The two expression vectors were transformed into embryogenic suspension cultures be derived from type II embryogenic culture according to the method of Green et al., *Molecular Genetics of Plants and Animals*, editors Downey et al., Academic Press, N.Y., 20, 147 (1983). The cultures were maintained in Murashige and Skoog ("MS") medium as described in Murashige et al., *Physio. Plant* 15: 453 (1962) supplemented with 2,4-dichlorophenoxyacetic acid (2,4-D) at 2 mg/L and sucrose at 30 g/L. The suspension cultures were passed through a 710 micron sieve 7 days prior to the experiment and the filtrate was maintained in MS medium.

Cells were harvested from the suspension culture by vacuum filtration on a Buchner funnel (Whatman No. 614), and 100 ml (fresh weight) of cells were placed in a 3.3 cm petri plate. The cells were dispersed in 0.5 mL fresh culture medium to form a thin layer of cells. The uncovered petri plate was placed in the sample chamber of a particle gun device manufactured by Biolistics Inc. (Geneva, N.Y.). A vacuum pump was used to reduce the pressure in the chamber to 0.1 atmosphere to reduce deceleration of the microparticles by air friction. The cells bombarded with tungsten particles having an average diameter of about 1.2 microns (GTE Sylvania Precision Materials Group, Towanda, Pa.). An equal mixture of PHI5168 and PHI610 were loaded onto the microparticles by adding 5 µl of a DNA solution (1 µg of DNA per 100 lamda) in TE buffer at pH 7.7 to 25 µl of a suspension of 50 mg of tungsten particles per ml distilled water in a 1.5 ml Eppendorf tube. The particles became aggregated and settled in the tube.

Cultures of transformed plant cells containing the foreign genes were cultivated for 4–8 weeks in 560R (medium) (N6-based medium with 1 mg/ml bialaphos). This medium selects for cells that express the bar gene.

Embryo formation was then induced in the embryogenic cultures and the cells germinated into plants. A two culture medium sequence was used to germinate somatic embryos observed on callus maintenance medium. Callus was transferred first to a culture medium (maturation medium) containing 5.0 mg/L indoleacetic acid (IAA) for 10 to 14 days while callus proliferation continued. Callus loading was at 50 mg per plate to optimize recovery per unit mass of material.

Callus was then transferred from "maturation" medium to a second culture medium containing a reduced level of IAA (1 mg/L) compared to the first culture medium. Cultures are placed in the light at this point. Germinating somatic embryos were characterized by a green shoot elongating with a connecting root access. Somatic embryos were then transferred to medium in a culture tube (150×25 mm) for an additional 10–14 days. At this time, the plants were about 7–10 cm tall, and were of sufficient size and vigor to be hardened to greenhouse conditions.

To harden regenerated plants, plants to be transferred to the growth chamber were removed from the sterile containers and solidified agar medium was rinsed off the roots. The plantlets were placed in a commercial potting mix in a growth chamber with a misting device for maintaining the relative humidity near 100% without excessively wetting the plant roots. After 3–4 weeks in the misting chamber the plants were robust enough for transplantation into field conditions.

Plants in the field were analyzed by observing male sterility. Selected plants were then further analyzed for presence of the avidin gene by PCR and Southern blotting, and for expression of avidin by ELISA, by standard methods.

Ninety four plants were analyzed by PCR, 53 of which were found to be fertile and 41 sterile. When the fertility of each plant was compared to presence of the avidin gene by PCR, a 98% correlation between presence of the gene and plant sterility was found. 5 plants were analyzed in detail for the presence of the avidin gene by Southern blotting. Three plants were shown to contain the avidin gene by Southern analysis. All three plants exhibited sterility. Two plants that did not have the avidin gene were completely fertile. There was thus a 100% correlation between the presence of the avidin gene and male sterility.

EXAMPLE 2

Use of Agrobacterium Strains Containing a Binary Vector Including a DNA Sequence Encoding Avidin to Generate Male Sterile Transgenic Soybean Plants A method for forming transgenic soybean plants is that described in U.S. patent application Ser. No. 07/920,409, now abandoned, which is hereby incorporated by reference. Soybean (*Glycine max*) seed, of Pioneer variety 9341, is surface sterilized by exposure to chlorine gas evolved in a glass bell jar. Gas is produced by adding 3.5 ml hydrochloric acid (34 to 37% w/w) to 100 ml sodium hypochlorite (5.25% w/w). Exposure is for 16 to 20 hours in a container approximately 1 cubic ft in volume. Surface sterilized seed is stored in petri dishes at room temperature. Seed is germinated by plating an 1/10 strength agar solidified medium according to Gambourg (B5 basal medium with minimal organics, Sigma Chemical Catalog No. G5893, 0.32 gm/L sucrose; 0.2% weight/volume 2-(N-morpholino) ethanesulfonic acid (MES), (3.0 mM) without plant growth regulators and culturing at 28° with a 16-hour day length and cool white fluorescent illumination of approximately 20 $\mu Em^{-2} S^{-1}$. After 3 or 4 days, seed is prepared for co-cultivation. The seed coat is removed and the elongating radical is removed 3 to 4 mm below the cotyledons.

Overnight cultures of *Agrobacterium tumefaciens* strain LBA4404 harboring a modified binary plasmid containing the avidin gene are grown to log phase in minimal A medium containing tetracycline, 1 µg/ml, and are pooled and an optical density measurement at 550 nm is taken. Sufficient volume of the culture is placed in 15 mL/conical centrifuge tubes such that upon sedimentation between 1 and $2 \times 10^{10}$ cells are collected in each tube with $10^9$ cells/ml. Sedimentation is by centrifugation at 6,000×g for 10 min. After centrifugation, the supernatant is decanted and the tubes are held at room temperature until inoculum is needed, but not longer than 1 hour.

Inoculations are conducted in batches such that each plate of seed is treated with a newly resuspended pellet of Agrobacterium. Bacterial pellets are resuspended individually in 20 ml inoculation medium, containing B5 salts (G5893), 3.2 g/L; sucrose, 2.0% w/v; 6-benzylaminopurine (BAP), 45 µm; indolebutyric-acid (IBA), 0.5 µM; acetosyringone (AS), 100 µM; buffered to pH 5.5 with MES 10 mM. Resuspension is achieved by vortexing. The inoculum is then poured into a petri dish containing prepared seed and the cotyledonary nodes are macerated with a surgical blade. This is accomplished by dividing seed in half by longitudinal section through the shoot apex, preserving the 2 whole cotyledons. The two halves of the shoot apex are then broken off their respective cotyledons by prying them away with a surgical blade. The cotyledonary node is then macerated with a surgical blade by repeated scoring along the axis of symmetry. Care is taken not to cut entirely through the explant to the axial side. Explants are prepared in roughly 5 minutes and then incubated for 30 minutes at room temperature with bacteria but without agitation. After 30 minutes, the explants are transferred into plates of the same medium solidified with Gelrite (Merck & Company Inc.), 0.2% w/v. Explants are embedded with adaxial side up and leveled with the surface of the medium and cultured at 22° C. for 3 days under cool white fluorescent light, approximately 20 $\mu$Em$^{-2}$ S$^{-1}$.

After 3 days, the explants are moved to liquid counterselection medium containing B5 salts (G5893), 3.2 g/l; sucrose, 2% w/v; BAP, 5 $\mu$M; IBA, 0.5 $\mu$M; vancomycin, 200 $\mu$g/ml; cefotaxime, 500 $\mu$g/ml, buffered to pH 5.7 with MES, 3 mM. Explants are washed in each petri dish with constant slow gyratory agitation at room temperature for 4 days. Counterselection medium is replaced 4 times.

The explants are then picked to agarose-solidified selection medium containing B5 salts (G5893), 3.2 g/l; sucrose, 2% w/v; BAP, 5.0 $\mu$M; IBA, 0.5 $\mu$M; kanamycin sulfate, 50 $\mu$g/ml; vancomycin, 100 $\mu$g/ml; cefotaxime, 30 $\mu$g/ml; timentin, 30 $\mu$g/ml, buffered to pH 5.7 with MES, 3 mM. Selection medium is solidified with Seakem Agarose, 0.3% w/v. The explants are embedded in the medium, adaxial side down and cultured at 28° with a 16 hour day length in cool white fluorescent illumination of 60 to 80 $\mu$Em$^{-2}$ S$^{-1}$.

After 2 weeks explants are again washed with liquid medium on the gyratory shaker. The wash is conducted overnight in counterselection medium containing kanamycin sulfate, 50 $\mu$g/ml. The following day, explants are picked to agarose/solidified selection medium. They are embedded in the medium adaxial side down and cultured for another 2 week period.

After 1 month on selection medium, transformed tissue is visible as green sectors of regenerating tissue against a background of bleached nonhealthy tissue. Explants without green sectors are discarded and explants with green sectors are transferred to elongation medium containing B5 salts (G5893), 3.2 g/l; sucrose, 2% w/v; IBA, 3.3 $\mu$M; gibberellic acid, 1.7 $\mu$M; vancomycin, 100 $\mu$g/ml; cefotaxime, 30 $\mu$g/ml; and timentin, 30 $\mu$g/ml, buffered to pH 5.7 with MES, 3 mM. Elongation medium is solidified with Gelrite, 0.2% w/v. The green sectors are embedded adaxial side up and cultured as before. Culture is continued on this medium with transfers to fresh plates every two weeks. When shoots are 0.5 cm in length they are excised at the base and placed in rooting medium in 13×100 ml test tubes. Rooting medium consists of B5 salts (G5893), 3.2 g/l; sucrose, 15 g/l; nicotinic acid, 20 $\mu$M; pyroglutamic acid (PGA), 900 mg/L and IBA, 10 $\mu$M. The rooting medium is buffered to pH 5.7 with MES, 3 mM and solidified with Gelrite at 0.2% w/v. After 1.0 days, the shoots are transferred to the same medium without IBA or PGA. Shoots are rooted and held in these tubes under the same environmental conditions as before.

When a root system is well established the plantlet is transferred to sterile soil. Temperature, photoperiod and light intensity remain the same as before.

The expression of avidin in transgenic soybean plants is confirmed and quantitated using ELISA, and presence of the gene is confirmed by PCR and Southern blotting. Stability of expression can be evaluated by these same methods over successive generations. Sterility problems are found to correlated with expression of avidin in the soybeans.

EXAMPLE 3

Preparation of Male Sterile Sunflower Plants by Expression of Avidin

An expression cassette encoding avidin is used to generate transgenic sunflower plants and seeds. The DNA sequence coding for avidin is inserted into an expression cassette under control of the ubiquitin promoter. This expression cassette is then subcloned into a binary vector such as PHI 5765 using the EcoR1 site. The binary vector is then transferred into an *Agrobacterium tumefaciens* helper strain.

Sunflower plants are transformed with Agrobacterium strain LBA4404 after microparticle bombardment as described by Bidney et al., *Plant Mol. Biol.* 18: 301 (1992). Briefly, seeds of Pioneer Sunflower Line SMF-3 are dehulled and surface sterilized. The seeds are imbibed in the dark at 26° C. for 18 hours on filter paper moistened with water. The cotyledons and root radical are removed and meristem explants cultured on 374BGA medium (MS salts, Shephard vitamins, 40 mg/L adenine sulfate, 3% sucrose, 0.8% phytagar pH 5.6 plus 0.5 mg/L of BAP, 0.25 mg/L, IAA and 0.1 mg/L GA). Twenty-four hours later, the primary leaves are removed to expose the apical meristem and the explants are placed with the apical dome facing upward in a 2 cm circle in the center of a 60 mm by 20 mm petri plate containing water agar. The explants are bombarded twice with tungsten particles suspended in TE buffer or with particles associated with an expression plasmid containing the avidin gene. The meristem explants are co-cultured on 374BGA medium in the light at 26° C. for an additional 72 hours of co-culture.

Agrobacterium treated meristems are transferred following the 72 hour co-culture period to medium 374 (374BGA with 1% sucrose and no BAP, IAA or GA$_3$) and supplemented with 250 $\mu$g/ml cefotaxime. The plantlets are allowed to develop for an additional 2 weeks under 16 hour day and 26° C. incubation conditions to green or bleach. Plantlets are transferred to medium containing kanamycin and allowed to grow. The presence of avidin in the plants is confirmed and quantitated as described in Example 2. The presence of male sterility is found to correlate with expression of avidin by the plants.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims. All publications and patent applications mentioned in this specification are indicative of the level of skill of those in the art to which the invention pertains.

What is claimed is:

1. An isolated DNA molecule comprising an anther-specific promoter operably linked to a nucleotide sequence encoding avidin.

2. An expression vector comprising the isolated DNA molecule of claim 1.

3. A transgenic plant wherein said plant comprises said expression vector of claim 2.

4. The transgenic plant of claim 3, wherein said plant is selected from the group consisting of corn, soybean and sunflower.

5. The expression vector of claim 2, wherein a nucleotide sequence encoding a signal sequence is operably linked to said nucleotide sequence encoding avidin.

6. The expression vector of claim 5, wherein said signal sequence is the barley alpha-amylase signal sequence.

7. A method of producing a transgenic male-sterile plant comprising introducing into plant cells an expression vector comprising a plant-compatible promoter operably linked to a nucleotide sequence encoding avidin and regenerating a transgenic plant from said transformed cells, wherein said promoter controls the expression of said avidin gene, and whereby said avidin gene expression causes male sterility of said transgenic plant.

8. The method of claim 7, wherein said promoter comprises a constitutive promoter.

9. The method of claim 8, wherein said constitutive promoter comprises a ubiquitin promoter.

10. The method of claim 9, wherein a nucleotide sequence encoding a signal sequence is operably linked to said nucleotide sequence encoding avidin.

11. The method of claim 10, wherein said signal sequence is the barley alpha-amylase signal sequence.

12. The method of claim 7, wherein said plant is selected from the group consisting of maize, sunflower and soybean.

13. The method of claim 7, wherein said promoter comprises a tissue-specific promoter.

14. The method of claim 13, wherein said promoter comprises an anther-specific promoter.

15. A method of using an avidin gene to produce a male-fertile hybrid plant, comprising the steps of:
   (a) producing a first parent male-sterile plant comprising a DNA molecule comprising a plant-compatible promoter operably linked to a nucleotide sequence encoding avidin wherein the expression of said avidin causes male sterility;
   (b) producing a second transgenic parent plant expressing a second foreign gene; and
   (c) cross-fertilizing said first parent with said second parent to produce a hybrid plant,
   wherein said hybrid plant expresses said second foreign gene, and wherein the product of said second foreign gene reduces expression of avidin in said hybrid plant, thereby producing a male-fertile hybrid plant.

16. The method of claim 15, wherein said second foreign gene is an antisense gene.

17. The method of claim 16, wherein said antisense gene is an avidin antisense gene.

18. The method of claim 15, wherein said DNA molecule of said first parent plant further comprises a LexA operator which is operatively linked to said promoter, and wherein said second foreign gene is the LexA repressor gene.

19. The expression vector of claim 2, wherein said anther-specific promoter sequence comprises an anther box selected from the group consisting of:
   (a) a DNA molecule having the nucleotide sequence of SEQ ID NO:1;
   (b) a DNA molecule having the nucleotide sequence of SEQ ID NO:2;
   (c) a DNA molecule having the nucleotide sequence of SEQ ID NO:3; and
   (d) a functional fragment of (a), (b) or (c).

20. The expression vector of claim 19, wherein said anther box has the nucleotide sequence of SEQ ID NO:1, and wherein said anther-specific promoter further comprises a core promoter selected from the group consisting of:
   (a) CaMV 35S core promoter;
   (b) a DNA molecule having the nucleotide sequence of SEQ ID NO:4;
   (c) a DNA molecule having the nucleotide sequence of SEQ ID NO:5;
   (d) a DNA molecule having the nucleotide sequence of SEQ ID NO:6; and
   (e) a functional fragment of (b), (c) or (d).

21. The expression vector of claim 19, wherein said anther box has the nucleotide sequence of SEQ ID NO:2, and wherein said anther-specific promoter further comprises a core promoter selected from the group consisting of:
   (a) CaMV 35S core promoter;
   (b) a DNA molecule having the nucleotide sequence of SEQ ID NO:4;
   (c) a DNA molecule having the nucleotide sequence of SEQ ID NO:5;
   (d) a DNA molecule having the nucleotide sequence of SEQ ID NO:6; and
   (e) a functional fragment of (b), (c) or (d).

22. The expression vector of claim 19, wherein said anther box has the nucleotide sequence of SEQ ID NO:3, and wherein said anther-specific promoter further comprises a core promoter selected from the group consisting of:
   (a) CaMV 35S core promoter;
   (b) a DNA molecule having the nucleotide sequence of SEQ ID NO:4;
   (c) a DNA molecule having the nucleotide sequence of SEQ ID NO:5;

(d) a DNA molecule having the nucleotide sequence of SEQ ID NO:6; and (e) a functional fragment of (b), (c) or (d).

23. A method for restoring fertility in a plant rendered male sterile by expression of avidin or streptavidin comprising spraying said plant with a solution of biotin.

24. The method of claim 15, wherein said plant-compatible promoter operably linked to the avidin gene is a constitutive promoter.

25. The method of claim 15, wherein said plant-compatible promoter is a tissue-specific promoter.

26. The method of claim 25, wherein said tissue-specific promoter is an anther-specific promoter.

27. The method of claim 15, wherein a nucleotide sequence encoding a signal sequence is operably linked to said nucleotide sequence encoding avidin.

28. The method of claim 27, wherein said signal sequence is the barley alpha-amylase signal sequence.

29. The method of claim 16, wherein said antisense gene is operably linked to an inducible promoter.

30. A method for producing seeds having a desired grain trait comprising the steps of:

(a) producing a first parent plant which is male-sterile and comprises a nucleotide sequence encoding avidin operably linked to a plant-compatible promoter sequence;

(b) producing a second parent plant which is male fertile and carries one or more genes controlling said desired grain trait;

(c) cross-fertilizing said first parent with said second parent to produce hybrid seeds with said grain trait; and (d) harvesting said seeds.

31. The method of claim 30, wherein said first parent plant is a hybrid plant.

32. The method of claim 30, wherein said grain trait is selected from the group consisting of oil, protein and starch content.

33. The method of claim 30, wherein said first and second plant is selected from the group consisting of corn, soybean, canola and sunflower.

34. The method of claim 33, wherein said first and second plant is corn.

35. The method of claim 33, wherein said first and second plant is soybean.

36. The method of claim 33, wherein said first and second plant is sunflower.

37. The method of claim 30, wherein said plant-compatible promoter sequence is an anther-specific promoter sequence comprising an anther box selected from the group consisting of:

(a) a DNA molecule having the nucleotide sequence of SEQ ID NO:1;

(b) a DNA molecule having the nucleotide sequence of SEQ ID NO:2;

(c) a DNA molecule having the nucleotide sequence of SEQ ID NO:3; and (d) a functional fragment of (a), (b) or (c).

38. The method of claim 37, wherein said anther box has the nucleotide sequence of SEQ ID NO:1, and wherein said anther-specific promoter further comprises a core promoter selected from the group consisting of:

(a) CaMV 35S core promoter;

(b) a DNA molecule having the nucleotide sequence of SEQ ID NO:4;

(c) a DNA molecule having the nucleotide sequence of SEQ ID NO:5;

(d) a DNA molecule having the nucleotide sequence of SEQ ID NO:6; and (e) a functional fragment of (b), (c) or (d).

39. The method of claim 37, wherein said anther box has the nucleotide sequence of SEQ ID NO:2, and wherein said anther-specific promoter further comprises a core promoter selected from the group consisting of:

(a) CaMV 35S core promoter;

(b) a DNA molecule having the nucleotide sequence of SEQ ID NO:4;

(c) a DNA molecule having the nucleotide sequence of SEQ ID NO:5;

(d) a DNA molecule having the nucleotide sequence of SEQ ID NO:6; and (e) a functional fragment of (b), (c) or (d).

40. The method of claim 37, wherein said anther box has the nucleotide sequence of SEQ ID NO:3, and wherein said anther-specific promoter further comprises a core promoter selected from the group consisting of:

(a) CaMV 35S core promoter;

(b) a DNA molecule having the nucleotide sequence of SEQ ID NO:4;

(c) a DNA molecule having the nucleotide sequence of SEQ ID NO:5;

(d) a DNA molecule having the nucleotide sequence of SEQ ID NO:6; and (e) a functional fragment of (b), (c) or (d).

41. The isolated DNA molecule of claim 1, wherein said avidin is streptavidin.

42. The methods of claims 7, 15 or 30 wherein said avidin is streptavidin.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:1:

```
GCGGCCGCGG ATCCGCTCAT CTGCTCGGTA CCAACCAGCC TTTCCTATTA CCATGCACAG      60

ATCT                                                                  64
```

(2) INFORMATION FOR SEQ ID NO:2:

(i) SEQUENCE CHARACTERISTICS:
        (A) LENGTH: 94 base pairs
        (B) TYPE: nucleic acid
        (C) STRANDEDNESS: single
        (D) TOPOLOGY: linear (xi) SEQUENCE DESCRIPTION: SEQ ID NO:2:

```
ACAGTTCACT AGATATGCAT GATCTTTAAC AATTGCTGCT GGATTGTGCG GTTTCTTTTG      60

GCACAAATGG CATGAACAGA GTAATCCGGG ACGC                                 94
```

(2) INFORMATION FOR SEQ ID NO:3:

(i) SEQUENCE CHARACTERISTICS:
        (A) LENGTH: 136 base pairs
        (B) TYPE: nucleic acid
        (C) STRANDEDNESS: single
        (D) TOPOLOGY: linear (xi) SEQUENCE DESCRIPTION: SEQ ID NO:3:

```
GCGGCCGCGG ATCCTGGCTG GATGAAACCG ATGCGAGAGA AGAAAAAAAA ATTGTTGCAT      60

GTAGTTGGCG CCTGTCACCC AACCAAACCA GTAGTTGAGG CACGCCCTGT TGCTCACGA     120

TCACGAACGT AGATCT                                                   136
```

(2) INFORMATION FOR SEQ ID NO:4:

(i) SEQUENCE CHARACTERISTICS:
        (A) LENGTH: 142 base pairs
        (B) TYPE: nucleic acid
        (C) STRANDEDNESS: single
        (D) TOPOLOGY: linear (xi) SEQUENCE DESCRIPTION: SEQ ID NO:4:

```
AGATCTAAGT AAGGTATATA TGTGCATAGT CTCCTAATTC TTCATCTTCA ACCTCTAGCT      60

GATTGATCTC TGGTATTTAC CACTCTTTCC TTCCTTCCTT CCTTCAATTC TAAATACCAC     120

AAATCAAAGT TGCTTTGCCA TG                                            142
```

(2) INFORMATION FOR SEQ ID NO:5:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:5:

```
ATCTCACCCT ATTAATACCA TGCTGACGAG CCAATAGC                             38
```

(2) INFORMATION FOR SEQ ID NO:6:

(i) SEQUENCE CHARACTERISTICS:
    (A) LENGTH: 107 base pairs
    (B) TYPE: nucleic acid
    (C) STRANDEDNESS: single
    (D) TOPOLOGY: linear (xi) SEQUENCE DESCRIPTION: SEQ ID NO:6:

AGATCTCTAT AAAACACGCA GGGACTGGAA AGCGAGATTT CACAGCTGAA AGCAGCCAAA          60

ACGCAGAAGC TGCACTGCAT ACATCGAGCT AACTATCTGC AGCCATG                      107